US00PP08268P

United States Patent [19]

Forde

[11] Patent Number: Plant 8,268

[45] Date of Patent: Jun. 22, 1993

[54] TULARE WALNUT TREE

[75] Inventor: Harold I. Forde, Davis, Calif.

[73] Assignee: The Regents of the University of California, Berkeley, Calif.

[21] Appl. No.: 759,009

[22] Filed: Sep. 12, 1991

[51] Int. Cl.[5] ..... A01H 5/00

[52] U.S. Cl. ..... Plt./32

[58] Field of Search ..... Plt./32

*Primary Examiner*—James R. Feyrer

[57] ABSTRACT

A new and distinct cultivar of walnut (*Juglans regia*) characterized in having semi-upright growth, good vigor and excellent production in high density (hedgerow) plantings. The medium textured, light colored shell is well-sealed and nearly round (36×40 mm). The light colored kernel weighs an average of 7.1 grams and makes up over 53 percent of the nut weight. This cultivar is especially well-suited to hedgerow plantings.

2 Drawing Sheets

DESCRIPTION

This invention relates to a new and distinct cultivar of walnut tree, named 'Tulare', botanical classification *Juglans regia.* The original tree grew from a seed from the University of California walnut breeding program in 1967.

A continuous walnut breeding program has been maintained at the University of California from 1948 until the present, with substantial support and/or personnel from the U.S. Department of Agriculture, Agricultural Research Service from 1982 on. In 1966, pistillate flowers of the cultivar 'Tehama' were bagged and pollinated with pollen from the cultivar 'Serr'. This selection grew from one of the resulting seeds, therefore, the parents of this selection are 'Tehama' and 'Serr'. 'Tehama' and 'Serr' were released as cultivars from the University of California Breeding Program by E. F. Serr and H. I. Forde in 1968. 'Tehama' resulted from crossing 'Waterloo'×'Payne' in 1957. 'Serr' resulted from the cross P.I. 159568×'Payne' in 1958.

Twenty-one seedlings of the cross 'Tehama'×'Serr' were established in the test orchard on the campus of the University of California, Davis. These seedlings were maintained under careful and coninuous observation. When such seedlings bore fruit, one which is the instant cultivar, identified as 67-11, evidenced novel and commercially desirable characteristics and was selected for asexual reproduction to permit further testing and possible introduction to the trade.

After its origin, as above, this selection was asexually reproduced by grafting in 1973 on seedlings of the two common rootstocks, Northern California black walnut *Juglans hindsii* and Paradox *J. hindsii*×*J. regia,* in the University of California (Department of Pomology) experimental orchard. Subsequently, it was also asexually propagated by grafting and budding in test plots in some of the walnut growing areas of California. The trees, leaves and fruit resulting from such reproductions all ran true to the parent trees in every respect.

In the photographs:

Figure 1:
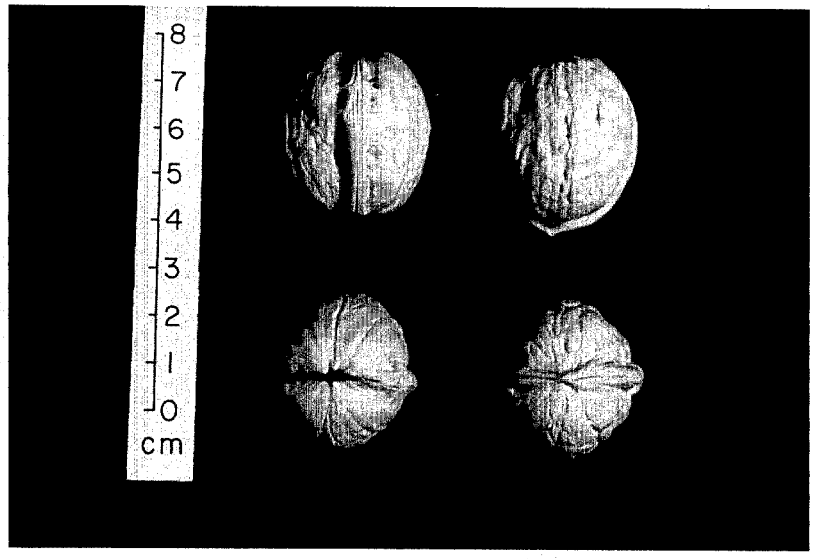
FIG. 1 illustrates four views of nuts in the shell which are typical of the new cultivar.
Figure 2:
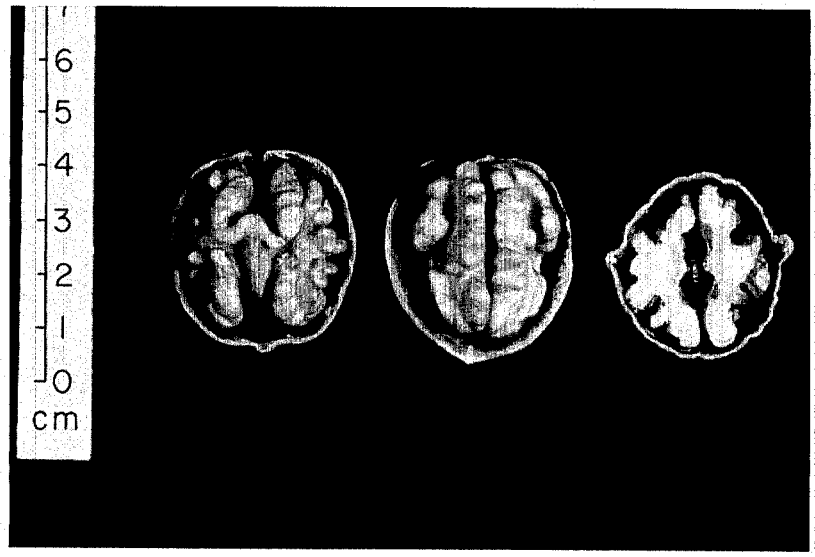
FIG. 2 illustrates the nut in cross section and in longitudinal view with half the shell removed at the suture and perpendicular to the suture.
Figure 3:
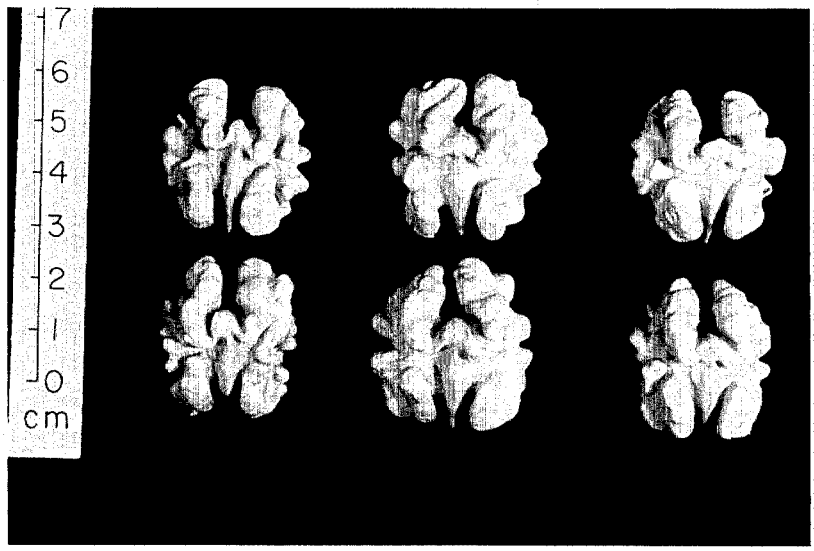
FIG. 3 illustrates kernel halves of the nut of the new cultivar.
Figure 4:
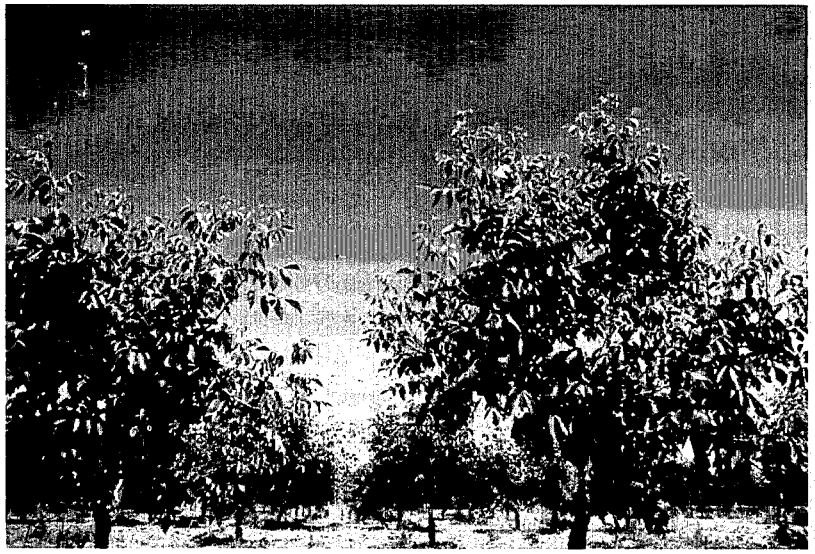
FIG. 4 illustrates a view of a specimen of a tree typical of the new cultivar.

This new and distinct cultivar of walnut tree named 'Tulare', previously described as selection 67-11, is characterized by its semi-upright growth, good vigor, good bloom overlap, and early and heavy production. Nearly all shoots from terminal buds and over 75 percent of the shoots from axillary buds produce pistillate flowers. The start of growth and leafing is about 12 days after 'Payne' and male and female bloom and harvest dates are about 6–10 days after 'Payne'. Male bloom consistently overlaps pink female bloom in mature trees and covers an average of 80 percent of the entire female bloom period.

Table 1 below compares the vigor and growth habit of 'Tulare' (67-11) with 14 other cultivars grown together in Tulare county, California. In its 4th, 5th, and 6th leaf 'Tulare' had 5 to 6 feet, 4 to 6 feet, and less than 4 feet of new growth per shoot, respectively. Among other cultivars it ranked near the top in vigor in early evaluations but slowed down in the 6th leaf, probably due to its high nut yield. Branch angle is less than 45°, making it an upright tree suitable to high density (hedgerow) plantings.

TABLE 1

FOURTH LEAF VEGETATIVE GROWTH RATINGS OF WALNUT CULTIVARS IN HEDGEROW CONFIGURATION[1]

| | Vigor[2] | | | | Uprightness[3] | | | |
|---|---|---|---|---|---|---|---|---|
| | Replicate | | | | Replicate | | | |
| | 1 | 2 | 3 | $\bar{X}$ | 1 | 2 | 3 | $\bar{X}$ |
| Amigo | 2.88 | 3.67 | 4.33 | 3.63 | 1.38 | 1.67 | 2.75 | 1.93 |
| Payne | 3.00 | 3.67 | 3 57 | 3.41 | 1.60 | 2.33 | 1.43 | 1.79 |
| Serr | 4.50 | 4.57 | 3.71 | 4.26 | 1.25 | 2.56 | 2.00 | 1.94 |
| Ashley | 3.80 | 4.43 | 3.50 | 3.91 | 1.50 | 2.86 | 2.13 | 2.16 |
| Chico | 3.00 | 3.20 | 3.43 | 3.21 | 1.00 | 1.00 | 1.29 | 1.10 |
| Vina | 2.50 | 3.20 | 3.30 | 3.00 | 1.50 | 2.10 | 2.25 | 1.95 |
| 67-13 | 3.50 | 3.71 | 3.60 | 3.60 | 1.88 | 2.00 | 1.20 | 1.69 |
| Tehama | 3.50 | 4.57 | 4.43 | 4.17 | 1.88 | 2.15 | 2.57 | 2.20 |
| Hartley | 4.29 | 3.40 | 3.66 | 3.78 | 2.71 | 1.40 | 2.16 | 2.09 |
| 67-11 | 4.14 | 4.00 | 4.11 | 4.08 | 1.43 | 1.00 | 1.77 | 1.40 |
| 68-104 | 3.66 | 3.43 | 3.33 | 3.47 | 2.00 | 1.14 | 1.55 | 1.56 |
| Howard | 3.75 | 4.00 | 3.33 | 3.69 | 1.50 | 2.13 | 1.17 | 1.60 |
| Chandler | 3.11 | 3.60 | 3.57 | 3.43 | 1.22 | 1.00 | 1.43 | 1.22 |
| Pedro | 3.38 | 3.66 | 4.00 | 3.68 | 1.50 | 1.66 | 1.66 | 1.61 |

TABLE 1-continued

| | | | | | | | | |
|---|---|---|---|---|---|---|---|---|
| Sunland | 4.43 | 4.20 | 4.16 | 4.26 | 2.43 | 2.60 | 2.00 | 2.34 |

[1]Ratings made 7-3-85.
Only trees on *J. hindsii* rootstock included.
Data represent averages of approximately 9 trees per replicate
[2]Vigor:
1 = <2' new growth per shoot
2 = 2-3' new growth per shoot
3 = 3-4' new growth per shoot
4 = 5-6' new growth per shoot
5 = >6' new growth per shoot
[3]Uprightness:
1 = normal (upright)
2 = some "willowing" of new growth
3 = excessive willowing of new growth FIFTH LEAF VEGETATIVE GROWTH RATINGS OF WALNUT CULTIVARS IN HEDGEROW CONFIGURATION - September, 1986[1]

| | Vigor[2] | | | | Willowiness[3] | | | |
|---|---|---|---|---|---|---|---|---|
| | Replicate | | | | Replicate | | | |
| | 1 | 2 | 3 | $\bar{X}$ | 1 | 2 | 3 | $\bar{X}$ |
| Amigo | 2.0 | 1.9 | 1.7 | 1.87 | 1.4 | 1.5 | 1.5 | 1.47 |
| Payne | 1.9 | 1.9 | 1.8 | 1.87 | 1.6 | 2.2 | 2.2 | 2.00 |
| Serr | 2.9 | 2.7 | 2.5 | 2.70 | 2.2 | 2.4 | 2.2 | 2.27 |
| Ashley | 2.1 | 2.0 | 1.9 | 2.00 | 2.5 | 2.4 | 2.4 | 2.43 |
| Chico | 1.5 | 1.5 | 1.6 | 1.53 | 1.1 | 1.2 | 1.4 | 1.23 |
| Vina | 1.5 | 2.1 | 1.9 | 1.83 | 2.1 | 2.5 | 2.6 | 2.40 |
| 67-13 | 1.7 | 1.9 | 1.9 | 1.83 | 1.4 | 1.9 | 1.9 | 1.73 |
| Tehama | 2.2 | 2.0 | 2.6 | 2.27 | 2.1 | 2.2 | 2.1 | 2.13 |
| Hartley | 2.1 | 1.6 | 2.4 | 2.03 | 2.1 | 2.0 | 2.4 | 2.17 |
| 67-11 | 2.8 | 2.4 | 1.8 | 2.33 | 2.1 | 1.9 | 1.9 | 1.97 |
| 68-104 | 2.5 | 1.6 | 1.9 | 2.00 | 1.9 | 1.9 | 2.1 | 1.97 |
| Howard | 1.1 | 1.0 | 1.2 | 1.10 | 1.4 | 1.1 | 1.3 | 1.27 |
| Chandler | 1.9 | 1.9 | 1.8 | 1.87 | 1.6 | 1.8 | 1.7 | 1.70 |
| Pedro | 1.7 | 2.1 | 1.3 | 1.70 | 1.6 | 2.3 | 1.9 | 1.93 |
| Sunland | 2.2 | 2.6 | 1.9 | 2.23 | 2.3 | 2.9 | 2.3 | 2.50 |

[1]Ratings made 9-17-86.
Data represent averages of approximately 9 trees per replicate
[2]Vigor: 1
1 = <4' average current season'shoot growth
2 = 4'-6' average current season'shoot growth
3 = >6' average current season'shoot growth
[3]Willowiness:
1 = <45° average angle of current season's shoot growth
2 = 45°-90° average angle of current season's shoot growth
3 = >90° average angle of current season'shoot growth SIXTH LEAF VEGETATIVE GROWTH RATINGS OF WALNUT CULTIVARS IN HEDGEROW CONFIGURATION 1 VISALIA 7/10/87[1]

| Cultivar | Vigor[2] | Uprightness[3] |
|---|---|---|
| Amigo | 1.22 | 1.67 |
| Payne | 1.22 | 1.89 |
| Serr | 2.33 | 2.00 |
| Ashley | 1.67 | 2.33 |
| Chico | 1.00 | 1.00 |
| Vina | 1.78 | 2.33 |
| 67-13 | 1.22 | 1.00 |
| Tehama | 2.00 | 2.00 |
| Hartley | 2.11 | 2.11 |
| 67-11 | 1.55 | 1.33 |
| 68-104 | 1.33 | 1.44 |
| Howard | 1.00 | 1.33 |
| Chandler | 1.78 | 1.67 |
| Pedro | 1.44 | 2.00 |
| Sunland | 2.22 | 2.00 |

[1]Data represent mean of 3 replicates of 9 trees
shoots terminated growth by this date
only side of tree hedged 1986/87 (north side) rated
[2]Vigor:
1 = <4' average new shoot growth
2 = 4'-6' average new shoot growth
3 = >6' average new shoot growth
[3]Uprightness:
1 = <45° average new shoot attitude
2 = 45°-90° average new shoot attitude
3 = >90° average new shoot attitude In a hedgerow trial (10'×20') grafted in 1983 in Tulare County, this cultivar ranked highest in yield compared with 15 other walnut cultivars in years 1987 through 1990 or 5th year from grafting on. In a similar trial (12'×24') of 13 cultivars grafted in 1985 in Yolo County this cultivar ranked highest in 1990, or 6th year from grafting.

'Tulare' is compared with its parents, 'Serr' and 'Tehama', in Table 2 below. 'Tulare' leafs out later than both parents but closer to 'Tehama' than 'Serr'. In male and female bloom dates it is similar to 'Tehama', usually falling within a few days. In catkin abundance 'Tulare' resembles 'Tehama' but has fewer catkins than 'Serr'. The latter is remarkable for its abundant catkin production. 'Tulare' is laterally fruitful like both parents, and in subjective yield estimates it is similar or better. Nut and kernel characteristics of the three cultivars are similar, although in general 'Serr' has a higher percent kernel, and 'Tulare' has lighter colored kernels. 'Tulare' does not exhibit severe pistillate flower abscission, a trait common in 'Serr'.

TABLE 2

| | Cultivars/ Selections (Parents) | Leafing Date | Leafing DAP[a] | Pollen Shedding 1st | Pollen Shedding Peak | Pollen Shedding Last | Pollen Shedding Abundance[b] |
|---|---|---|---|---|---|---|---|
| 1989 | Tehama (Payne X Waterloo) | 3/27 | 9 | 4/3 | 4/8 | 4/17 | 6 |
| | Serr (Payne X PI 159568) | 3/19 | 1 | 3/24 | 4/4 | 4/9 | 8 |
| | Tulare (Tehama X Serr) | 3/30 | 12 | 4/2 | 4/9 | 4/22 | 6 |
| 1990 | Tehama (Payne X Waterloo) | 3/23 | 5 | 3/27 | 4/2 | 4/14 | 7 |
| | Serr (Payner X PI 159568) | 3/19 | 1 | 3/24 | 3/28 | 4/6 | 8 |
| | Tulare (Tehama X Serr) | 3/25 | 7 | 3/30 | 4/4 | 4/19 | 7 |
| 1991 | Tehama (Payne X Waterloo) | 3/23 | 16 | 4/5 | 4/11 | 4/20 | 6 |
| | Serr (Payne X PI 159568) | 3/10 | 3 | 3/22 | 3/31 | 4/12 | 8 |
| | Tulare (Tehama X Serr) | 3/27 | 20 | 4/6 | 4/10 | 4/22 | 6 |

| | Cultivars/ Selections (Parents) | Pistillate Bloom 1st | Pistillate Bloom Peak | Pistillate Bloom Last | Fruitful Laterals | Yield[c] | Blight[d] |
|---|---|---|---|---|---|---|---|
| 1989 | Tehama (Payne X Waterloo) | 4/8 | 4/13 | 4/20 | 75 | 5 | 5 |
| | Serr (Payne X PI 159568) | 4/3 | 4/9 | 4/14 | 60 | 6 | 5 |
| | Tulare (Tehama X Serr) | 4/8 | 4/14 | 4/23 | 60 | 6 | 4 |
| 1990 | Tehama (Payne X Waterloo) | 4/6 | 4/14 | 4/21 | 50 | 6 | 3 |
| | Serr (Payne X PI 159568) | 3/30 | 4/3 | 4/10 | 50 | 4 | 2 |
| | Tulare (Tehama X Serr) | 4/7 | 4/13 | 4/21 | 75 | 6 | 2 |
| 1991 | Tehama (Payne X Waterloo) | 4/7 | 4/14 | 4/22 | 50 | 6 | 2 |
| | Serr (Payne X PI 159568) | 4/1 | 4/5 | 4/13 | 90 | 6 | 0 |
| | Tulare (Tehama X Serr) | 4/10 | 4/14 | 4/23 | 80 | 6 | 2 |

[a]"DAP" denotes "days after Payne".
[b]Catkin abundance: 0 - no catkins, 9 - extremly dense catkin production.
[c]Yield estimate: 0 - no walnuts, 9 - extremly high yield.
[d]Blight score: 0 - no sign of infection, 9 - extremly severe infestation.

| Cultivars/ Selections | Harvest | Shell[b] | Shell[c] | Shell Thickness |
|---|---|---|---|---|

TABLE 2-continued

| | (Parents) | Date | DAP[a] | Seal | Strength | (mm) |
|---|---|---|---|---|---|---|
| 1989 | Tehama (Payne X Waterloo) | 9/17 | 2 | 0 | 2 | 1.6 |
| | Serr (Payne X PI 159568) | 9/17 | 2 | 0 | 1 | 1.5 |
| | Tulare (Tehama X Serr) | 9/19 | 4 | 0 | 2 | 1.6 |
| 1990 | Tehama (Payne X Waterloo) | 9/16 | 1 | 0 | 2 | 1.4 |
| | Serr (Payne X PI 159568) | 9/14 | −1 | 0 | 1 | 1.5 |
| | Tulare (Tehama X Serr) | 9/19 | 4 | 0 | 2 | 1.3 |
| 1991 | Tehama (Payne X Waterloo) | 9/26 | 7 | 0 | 2 | 1.4 |
| | Serr (Payne X PI 159568) | 9/24 | 5 | 0 | 2 | 1.5 |
| | Tulare (Tehama X Serr) | 10/1 | 12 | 0 | 2 | 1.2 |

| | Cultivars/ Selections (Parents) | Avg. Weight In-Shell (gms) | Avg. Weight Kernel (gms) | % KERNEL | Kernel[d] Fill Grade |
|---|---|---|---|---|---|
| 1989 | Tehama (Payne X Waterloo) | 12.23 | 6.57 | 49.6 | 4 |
| | Serr (Payne X PI 159568) | 10.60 | 5.94 | 56.0 | 4 |
| | Tulare (Tehama X Serr) | 13.98 | 7.28 | 52.0 | 4 |
| 1990 | Tehama (Payne X Waterloo) | 11.63 | 6.01 | 51.6 | 4 |
| | Serr (Payner X PI 159568) | 15.69 | 8.98 | 57.2 | 3 |
| | Tulare (Tehama X Serr) | 14.11 | 7.81 | 55.3 | 4 |
| 1991 | Tehama (Payne X Waterloo) | 15.91 | 8.20 | 51.5 | 4 |
| | Serr (Payne X PI 159568) | 14.59 | 8.08 | 55.3 | 4 |
| | Tulare (Tehama X Serr) | 16.51 | 9.03 | 54.6 | 5 |

| | Cultivars/ Selections (Parents) | Kernel Color (%)e Light | Light Amber | Amber |
|---|---|---|---|---|
| 1989 | Tehama (Payne X Waterloo) | 100 | 0 | 0 |
| | Serr (Payne X PI 159568) | 90 | 0 | 10 |
| | Tulare (Tehama X Serr) | 90 | 10 | 0 |
| 1990 | Tehama (Payne X Waterloo) | 90 | 10 | 0 |
| | Serr (Payner X PI 159568) | 90 | 10 | 0 |
| | Tulare (Tehama X Serr) | 100 | 0 | 0 |
| 1991 | Tehama (Payne X Waterloo) | 90 | 0 | 10 |
| | Serr (Payne X PI 159568) | 80 | 20 | 0 |
| | Tulare (Tehama X Serr) | 100 | 0 | 0 |

| | Cultivars/ Selections (Parents) | Kernel Shrivel (%)e Tip | <50 | ≧50 | Blank |
|---|---|---|---|---|---|
| 1989 | Tehama (Payne X Waterloo) | 0 | 0 | 0 | 0 |
| | Serr (Payne X PI 159568) | 0 | 0 | 20 | 10 |
| | Tulare (Tehama X Serr) | 10 | 0 | 0 | 0 |
| 1990 | Tehama (Payne X Waterloo) | 10 | 10 | 0 | 0 |
| | Serr (Payner X PI 159568) | 0 | 0 | 0 | 0 |
| | Tulare (Tehama X Serr) | 0 | 0 | 0 | 0 |
| 1991 | Tehama (Payne X Waterloo) | 0 | 0 | 0 | 10 |
| | Serr (Payne X PI 159568) | 0 | 0 | 0 | 0 |
| | Tulare (Tehama X Serr) | 50 | 0 | 0 | 0 |

[a]"DAP" denotes "days after Payne".
[b]Shell Seal: percent with open seal under slight pressure.
[c]Shell Strength: 1 - strong. 4 - very weak.
[d]Kernel Fill: 3 - well. 7 - poor.
[e]Kernel Color and Shrivel taken on 10 randomly selected nuts, other traits on ten sound nuts.

Compared with other cultivars recommended for hedgerows, 'Tulare' is substantially different from a) 'Chico' which has smaller nuts; b) 'Chandler' which requires a pollenizer because male and female flowering periods do not overlap; c) 'Howard' which is a smaller, less vigorous tree and also requires a pollenizer; and d) 'Vina' which has poorer nut quality and willowy growth.

It is the habit of the new cultivar that nearly all shoots from terminal buds and > than 75% of the lateral shoots produce one or two pistillate flowers. Advantageous precocity of 'Tulare' is indicated by pistillate flowers which usually appear in the second year from grafting. Exemplary dates of foliation, inflorescence and harvesting are given in Table 3 below. Yields from the fourth through the eighth leaf after grafting are shown in Table 4 below. 'Tulare' ranked higher in yield than 'Chico', 'Vina', 'Chandler' and 'Howard', the other cultivars heretofore recommended for high-density plantings. In a Yolo county trial, 'Tulare' ranked higher than those four in 1990 but lower than 'Chico' in 1989 and lower than either 'Chico' or 'Vina' in 1988.

TABLE 3

Comparison of 'Tulare' and 'Chico', 1981-90.

| Trait | Mean | Range |
|---|---|---|
| | Tulare | |
| Leafing date | 28 Mar. | 18 Mar.-9 Apr. |
| First female bloom | 7 Apr. | 27 Mar.-22 Apr. |
| Peak female bloom | 16 Apr. | 6-28 Apr. |
| Last female bloom | 25 Apr. | 19 Apr.-3 May |
| First pollen shed | 1 Apr. | 19 Mar.-18 Apr. |
| Last pollen shed | 22 Apr. | 11-29 Apr. |
| Harvest | 22 Sept. | 9 Sept.-4 Oct. |
| Laterial fruitfulness | 78% | 60%-90% |
| In-shell yield[z] | 6.0 | 5 -7 |
| In-shell wt (g) | 13.3 | 11.2-14.8 |
| Kernel wt (g) | 7.1 | 5.5-8.0 |
| Kernel (%) | 53.3 | 48.7-56.2 |
| Light-colored kernels | 75% | 30%-100% |
| Shell texture | Medium | Medium-rough |
| Shell color | Medium | Medium-dark |
| | Chico | |
| Leafing date | 17 Mar. | 6-24 Mar. |
| First female bloom | 23 Mar. | 11 Mar.-4 Apr. |
| Peak female bloom | 31 Mar. | 18 Mar.-18 Apr. |
| Last female bloom | 12 Apr. | 2-22 Apr. |
| First pollen shed | 4 Apr. | 24 Mar.-24 Apr. |
| Last pollen shed | 20 Apr. | 11-29 Apr. |
| Harvest | 214Sept. | 2-20 Sept. |
| Laterial fruitfulness | 91% | 70%-100% |
| In-shell yield[z] | 6.4 | 5-8 |
| In-shell wt (g) | 10.7 | 9.1-12.1 |
| Kernel wt (g) | 5.0 | 4.2-5.6 |
| Kernel (%) | 46.6 | 43.7-51.4 |
| Light-colored kernels | 69% | 50%-100% |
| Shell texture | Medium | Medium-smooth |
| Shell color | Medium | Medium-light |

[z]Based on a 0-9 scale, woth 9 being unusually high yield.

TABLE 4

In-shell nut yield of 'Tulare' walnut in comparison with 'Chandle', 'Howard', 'Chico', and 'Vina' from the fourth through the eighth leaf after grafting (1986–90) in Tulare County.

| | Yield (kg · ha$^{-1}$)[z] | | | | |
|---|---|---|---|---|---|
| Cultivar | 1986 | 1987 | 1988 | 1989 | 1990 |
| Tulare | 2500 bc[y] | 6490 a | 7770 a | 7100 a | 6830 a |
| Chico | 2920 ab | 5990 ab | 4650 b | 7060 a | 4010 b |
| Vina | 3090 ab | 4880 bc | 4760 b | 5490 b | 3960 b |
| Chandler | 3380 a | 4240 cd | 4340 b | 3180 c | 4990 b |
| Howard | 2010 c | 3390 d | 3900 b | 3430 c | 4650 b |

[z]Based on 519 trees/ha.
[y]Mean separation in columns by Duncan's multiple range test, P = 0.05.

The botanical details of this new and distinct cultivar follow. Data on phenology and nut and kernel characteristics were gathered in the University of California, Davis Pomology orchards, over a ten year period on four grafted trees beginning on the eighth year from grafting:

Tree: Size, medium (between 'Chandler' and 'Serr'); vigor, vigorous; growth, semi-upright tree, tends to be a little taller than it is wide; production, very productive; bearing, early regular bearer.

Trunk and branches: Like most other *J. regia.* Old bark, smooth, very old bark would probably roughen as it does in other walnuts. Like other walnuts, new shoots have green bark which turns brown as the season progresses, this is also like other walnuts.

Leaves: Leaves are pinnately compound with 5 to 9 leaflets per leaf. Leaves are similar in color to other walnuts with lower surface being lighter than the top.

Leaves vary in length from about 29 to 45 cm., averaging about 36 cm. Leaflets vary in length from about 4 to 16 cm. averaging about 11 cm., and in width from about 3 to 10 cm., averaging about 6 cm. The basal leaflets are smaller with the terminal leaflet and the leaflets next to it being the largest.

Leaflet shape is elliptic to elongated ovate. Leaflets have acute apices and rounded or uneven bases. Uneven bases have blade on one side of the mid-rib 2 to 5 mm. farther from the rachis than it is on the other side.

Leaf texture, smooth; margin, smooth; venation, pinnate.

Start of growth, leafing date, is mid-season having been 4 to 19 days after 'Payne', averaging 12 days after 'Payne'. This is practically the same leafing date as 'Hartley'.

Inflorescence: This cultivar is precocious, young grafted trees having produced pistillate flowers at two years of age and catkins at three. About 75 percent of the axillary (lateral) buds produce pistillate flowers.

The male flowers mature first and shed pollen for about three weeks beginning about one week after 'Payne' in late March or early April in Davis, Calif. Bloom of pistillate flowers starts about one week after the beginning of male bloom and continues for a few days after the end of male bloom. Peak female bloom occurs about one week after 'Payne'. Most flowering tips have two pistillate flowers. There is nothing distinctive about the form or color of the male or female flowers as they are similar to most other walnut flowers.

Harvest: Nuts of this cultivar are ready to harvest about 8 days after 'Payne' around the last week of September in Davis, Calif.

When 80 to 90% of the hulls have split the nuts are ready for harvesting by shaker. The cultivar responds to mechanical harvest in a manner similar to other commercial cultivars.

The Fruit: The green fruit before it is ready to harvest is almost spherical in shape being only 2–4 mm. longer than wide. The hull is similar in color to other walnuts and is of average thickness.

The Nut and the Shell: The shape of the nut is nearly round (36×40 mm.) and slightly flattened on the stem end. Nuts can be easily balanced on the stem end. Sutures protrude from the shoulder to the tip, slightly but not unusually. The nut separates cleanly from the hull as with other commercial cultivars.

The nut shell is medium light colored and has a medium texture. It is well-sealed, strong and about 1.5 mm thick. The kernel is of average plumpness and makes up about 53 percent of the whole nut weight. The average kernel weight is 7.1 grams, the nut about 13.3 grams. An average of 75 percent of the kernels are classified as light according to the U.S. Department of Agriculture grading chart.

Additional information on nut characteristics appear in Tables 5 and 6 below which list crack out data in comparison to other commercial cultivars.

TABLE 5

Cultivar and Selection Harvest Evaluations at U. C. Davis (Fall 1991)

| Cultivars/Selections (Cross) | Harvest Date | Harvest DAP[a] | 5 yr avg[b] |
|---|---|---|---|
| Reference | | | |
| PAYNE | 9/19 | 0 | 0 |
| HARTLEY | 10/17 | 28 | 20 |
| SCH FRANQUETTE | 10/19 | 40 | 35 |
| Established | | | |
| SERR (PAYNE X PI 159568) | 9/24 | 5 | 3 |
| ASHLEY | 9/20 | 1 | 0 |
| CHICO (SHARKEY X MARCHETTI) | 9/22 | 3 | 1 |
| SUNLAND (LOWPOC X PI 159568) | 10/8 | 19 | 15 |
| VINA (PAYNE X SCH FRANQUETTE | 9/25 | 6 | 5 |
| TEHAMA (PAYNE X WATERLOO) | 9/26 | 7 | 6 |
| AMIGO (SHARKEY X C. MAYETTE) | 9/17 | −2 | −1 |
| PEDRO (PAYNE X C. MAYETTE) | 10/6 | 17 | 11 |
| HOWARD (PEDRO X 56-224) | 9/25 | 6 | 6 |
| CHANDLER (PEDRO X 56-224) | 10/14 | 25 | 19 |
| CISCO (PEDRO X MEYLAN) | 10/19 | 3 | 0 24 |
| Selections | | | |
| TULARE, 67-011 (TEHAMA X SERR) | 10/1 | 12 | 9 |
| 67-013 (TEHAMA X SERR) | 9/24 | 5 | 1 |
| 72-013 (59-165 X 53-39) | | discontinued | |
| 72-036 (53-39 X CHICO) | — | — | 11[1] |
| 76-080 (CHANDLER X 61-25) | 10/18 | 29 | 14[4] |
| 77-010 (HOWARD X 64-57) | 9/29 | 10 | 3[2] |
| 77-012 (HOWARD X 64-57) | 9/27 | 8 | −1 |
| 78-010 (53-153 X CHANDLER) | — | — | 28[4] |

| Cultivars/Selections (Cross) | Shell[c] Seal | Shell[d] Strength | Shell Thick. (mm) |
|---|---|---|---|

TABLE 5-continued

Cultivar and Selection Harvest Evaluations at U. C. Davis (Fall 1991)

| | | | |
|---|---|---|---|
| Reference | | | |
| PAYNE | 0 | 2 | 1.6 |
| HARTLEY | 0 | 1 | 1.7 |
| SCH FRANQUETTE | 0 | 1 | 1.5 |
| Established | | | |
| SERR (PAYNE X PI 159568) | 0 | 2 | 1.5 |
| ASHLEY | 0 | 2 | 1.5 |
| CHICO (SHARKEY X MARCHETTI) | 0 | 1 | 1.7 |
| SUNLAND (LOWPOC X PI 159568) | 0 | 1 | 1.3 |
| VINA (PAYNE X SCH FRANQUETTE | 0 | 2 | 1.5 |
| TEHAMA (PAYNE X WATERLOO) | 0 | 2 | 1.3 |
| AMIGO (SHARKEY X C. MAYETTE) | 0 | 2 | 1.5 |
| PEDRO (PAYNE X C. MAYETTE) | 0 | 2 | 1.6 |
| HOWARD (PEDRO X 56-224) | 0 | 2 | 1.3 |
| CHANDLER (PEDRO X 56-224) | 0 | 3 | 1.2 |
| CISCO (PEDRO X MEYLAN) | 0 | 2 | 1.5 |
| Selections | | | |
| TULARE, 67-011 (TEHAMA X SERR) | 0 | 2 | 1.2 |
| 67-013 (TEHAMA X SERR) | 0 | 2 | 1.3 |
| 72-013 (59-165 X 53-39) | discontinued | — | — |
| 72-036 (53-39 X CHICO) | — | — | — |
| 76-080 (CHANDLER X 61-25) | 20 | 2 | 1.2 |
| 77-010 (HOWARD X 64-57) | 0 | 2 | 1.5 |
| 77-012 (HOWARD X 64-57) | 0 | 2 | 1.7 |
| 78-010 (53-153 X CHANDLER) | — | — | — |

| Cultivars/Selections (Cross) | Avg. Weight In-Shell (gms) | Avg. Weight Kernal (gms) | % Kernel 1991 | % Kernel 5 yr avg |
|---|---|---|---|---|
| Reference | | | | |
| PAYNE | 13.46 | 6.88 | 51.1 | 50.8 |
| HARTLEY | 17.36 | 8.43 | 48.5 | 46.4 |
| SCH FRANQUETTE | 13.93 | 7.28 | 52.2 | 48.9 |
| Established | | | | |
| SERR (PAYNE X PI 159568) | 14.59 | 8.07 | 55.3 | 56.7 |
| ASHLEY | 13.43 | 6.48 | 48.2 | 49.7 |
| CHICO (SHARKEY X MARCHETTI) | 11.65 | 5.48 | 46.9 | 46.9 |
| SUNLAND (LOWPOC X PI 159568) | 18.65 | 10.64 | 57.0 | 57.7 |
| VINA (PAYNE X SCH FRANQUETTE | 13.77 | 6.73 | 48.9 | 48.4 |
| TEHAMA (PAYNE X WATERLOO) | 15.90 | 8.20 | 51.5 | 49.5 |
| AMIGO (SHARKEY X C. MAYETTE) | 13.93 | 6.67 | 47.9 | 50.5 |
| PEDRO (PAYNE X C. MAYETTE) | 15.56 | 7.71 | 49.5 | 47.8 |
| HOWARD (PEDRO X 56-224) | 12.72 | 6.46 | 50.7 | 49.5 |
| CHANDLER (PEDRO X 56-224) | 12.93 | 6.94 | 53.6 | 50.0 |
| CISCO (PEDRO X MEYLAN) | 15.64 | 7.61 | 48.6 | 47.3 |
| Selections | | | | |
| TULARE, 67-011 (TEHAMA X SERR) | 16.51 | 9.03 | 54.6 | 52.9 |
| 67-013 (TEHAMA X SERR) | 17.80 | 10.44 | 58.6 | 55.9 |
| 72-013 (59-165 X 53-39) | — | — | — | 58.1[1] |
| 72-036 (53-39 X CHICO) | — | — | — | 59.0[1] |
| 76-080 (CHANDLER X 61-25) | 14.64 | 8.64 | 59.1 | 52.3[4] |
| 77-010 (HOWARD X 64-57) | 14.85 | 7.36 | 49.5 | 49.9[2] |
| 77-012 (HOWARD X 64-57) | 15.72 | 7.53 | 47.9 | 47.3 |
| 78-010 (53-153 X CHANDLER) | — | — | — | 46.2[4] |

| Cultivars/Selections (Cross) | Kernel[e] Fill Grade | Kernel Color (%)[f] Light | Light Amber | Amber |
|---|---|---|---|---|
| Reference | | | | |
| PAYNE | 4 | 100 | 0 | 0 |
| HARTLEY | 6 | 90 | 10 | 0 |
| SCH FRANQUETTE | 4 | 70 | 30 | 0 |
| Established | | | | |
| SERR (PAYNE X PI 159568) | 4 | 80 | 20 | 0 |
| ASHLEY | 5 | 100 | 0 | 0 |
| CHICO (SHARKEY X MARCHETTI) | 3 | 100 | 0 | 0 |
| SUNLAND (LOWPOC X PI 159568) | 4 | 80 | 20 | 0 |
| VINA (PAYNE X SCH FRANQUETTE | 5 | 90 | 0 | 10 |
| TEHAMA (PAYNE X WATERLOO) | 4 | 90 | 0 | 10 |
| AMIGO (SHARKEY X C. MAYETTE) | 5 | 100 | 0 | 0 |
| PEDRO (PAYNE X C. MAYETTE) | 5 | 90 | 10 | 0 |
| HOWARD (PEDRO X 56-224) | 5 | 100 | 0 | 0 |
| CHANDLER (PEDRO X 56-224) | 5 | 100 | 0 | 0 |
| CISCO (PEDRO X MEYLAN) | 5 | 100 | 0 | 0 |
| Selections | | | | |
| TULARE, 67-011 (TEHAMA X SERR) | 5 | 100 | 0 | 0 |
| 67-013 (TEHAMA X SERR) | 4 | 100 | 0 | 0 |
| 72-013 (59-165 X 53-39) | — | — | — | — |
| 72-036 (53-39 X CHICO) | — | — | — | — |
| 76-080 (CHANDLER X 61-25) | 4 | 100 | 0 | 0 |
| 77-010 (HOWARD X 64-57) | 5 | 90 | 10 | 0 |
| 77-012 (HOWARD X 64-57) | 5 | 80 | 20 | 0 |
| 78-010 (53-153 X CHANDLER) | — | — | — | — |

| Cultivars/Selections (Cross) | Kernel Shrivel (%)[f] Tip | <50 | 50 | Blank |
|---|---|---|---|---|
| Reference | | | | |
| PAYNE | 0 | 0 | 0 | 0 |
| HARTLEY | 0 | 0 | 0 | 0 |
| SCH FRANQUETTE | 0 | 10 | 0 | 0 |
| Established | | | | |
| SERR (PAYNE X PI 159568) | 0 | 0 | 0 | 0 |
| ASHLEY | 10 | 10 | 0 | 0 |
| CHICO (SHARKEY X MARCHETTI) | 0 | 0 | 0 | 0 |
| SUNLAND (LOWPOC X PI 159568) | 0 | 0 | 0 | 0 |
| VINA (PAYNE X SCH FRANQUETTE | 0 | 0 | 0 | 0 |
| TEHAMA (PAYNE X WATERLOO) | 0 | 0 | 0 | 10 |

TABLE 5-continued

| Cultivar and Selection Harvest Evaluations at U. C. Davis (Fall 1991) | | | | |
|---|---|---|---|---|
| AMIGO (SHARKEY X C. MAYETTE) | 20 | 20 | 0 | 0 |
| PEDRO (PAYNE X C. MAYETTE) | 0 | 0 | 0 | 0 |
| HOWARD (PEDRO X 56-224) | 0 | 0 | 0 | 0 |
| CHANDLER (PEDRO X 56-224) | 30 | 30 | 0 | 0 |
| CISCO (PEDRO X MEYLAN) | 0 | 0 | 0 | 0 |
| Selections | | | | |
| TULARE, 67-011 (TEHAMA X SERR) | 50 | 50 | 0 | 0 |
| 67-013 (TEHAMA X SERR) | 0 | 0 | 0 | 0 |
| 72-013 (59-165 X 53-39) | — | — | — | — |
| 72-036 (53-39 X CHICO) | — | — | — | — |
| 76-080 (CHANDLER X 61-25) | 30 | 30 | 0 | 0 |
| 77-010 (HOWARD X 64-57) | 20 | 20 | 0 | 0 |
| 77-012 (HOWARD X 64-57) | 0 | 0 | 0 | 0 |
| 78-010 (53-153 X CHANDLER) | — | — | — | — |

[a]"DAP" denotes "days after Payne".
[b]Superscripts indicate number of years for average, if 5 years of data not available.
[c]Shell Seal: percent with open seal under slight pressure.
[d]Shell Stength: 1 - strong, 4 - very weak.
[e]Kernel Fill: 3 - well, 7 - poor.
[f]Kernel Color and Shrivel taken on 10 randomly selected nuts, other traits on ten sound nuts.

TABLE 6

| 1991 UCD Cultivar/Selecton Evaluation | | | | |
|---|---|---|---|---|
| | Crack Test Kernal Yield (percent in-shell wt.) | | | |
| Cultivar/Selection | % Large Size | RLI[a] | Light | Light Amber |
| Reference | | | | |
| Payne | 100 | 52.2 | 49 | 1 |
| Hartley | 98 | 54.5 | 44 | 1 |
| S. Franquette | 99 | 52.4 | 39 | 5 |
| Established | | | | |
| Ashley | 100 | 51.8 | 42 | 5 |
| Chico | 46 | 54.1 | 40 | 3 |
| Serr | 100 | 50.0 | 47 | 7 |
| Sunland | 100 | 50.7 | 55 | 2 |
| Vina | 100 | 50.0 | 41 | 6 |
| Tehama | 99 | 53.2 | 46 | 1 |
| Amigo | 100 | 56.2 | 46 | 1 |
| Pedro | 100 | 52.1 | 44 | 2 |
| Howard | 100 | 53.9 | 49 | 0 |
| Chandler | 99 | 56.9 | 50 | 0 |
| Cisco (UC 66-178) | 100 | 54.1 | 47 | 0 |
| Selections | | | | |
| UC 67-011 ("Tulare") | 100 | 51.5 | 48 | 2 |
| UC 67-013 | 100 | 54.8 | 52 | 2 |
| UC 76-080 | 100 | 57.4 | 55 | 0 |
| UC 77-012 | 100 | 48.9 | 26 | 4 |

TABLE 6-continued

| 1991 UCD Cultivar/Selecton Evaluation | | | | |
|---|---|---|---|---|
| | Crack Test Kernal Yield (percent in-shell wt.) | | | |
| Cultivar/Selection | Amber | Total Edible | Off Grade | Total Yield |
| Reference | | | | |
| Payne | 0 | 50 | 0 | 50 |
| Hartley | 1 | 46 | 1 | 47 |
| S. Franquette | 6 | 50 | 2 | 52 |
| Established | | | | |
| Ashley | 2 | 49 | 1 | 50 |
| Chico | 1 | 44 | 1 | 45 |
| Serr | 0 | 54 | 1 | 55 |
| Sunland | 0 | 57 | 0 | 57 |
| Vina | 0 | 47 | 2 | 49 |
| Tehama | 0 | 47 | 2 | 49 |
| Amigo | 0 | 47 | 0 | 47 |
| Pedro | 2 | 48 | 0 | 48 |
| Howard | 1 | 50 | 0 | 50 |
| Chandler | 0 | 50 | 1 | 51 |
| Cisco (UC 66-178) | 0 | 47 | 0 | 47 |
| Selections | | | | |
| UC 67-011 ("Tulare") | 0 | 50 | 2 | 52 |
| UC 67-013 | 0 | 54 | 1 | 55 |
| UC 76-080 | 0 | 55 | 0 | 55 |
| UC 77-012 | 7 | 37 | 6 | 43 |

| | Internal Damage (Number) | | | |
|---|---|---|---|---|
| Cultivar/Selection | Shrivel | Other[b] | $/100 lb | Date |
| Reference | | | | |
| Payne | 0 | 0 | 71.74 | 9/19 |
| Hartley | 4 | 1 | 66.21 | 10/17 |
| S. Franquette | 3 | 1 | 66.58 | 10/29 |
| Established | | | | |
| Ashley | 1 | 2 | 64.39 | 9/20 |
| Chico | 2 | 2 | 59.48 | 9/22 |
| Serr | 1 | 1 | 71.09 | 9/24 |
| Sunland | 0 | 0 | 78.14 | 10/8 |
| Vina | 2 | 3 | 57.69 | 9/25 |
| Tehama | 3 | 2 | 63.16 | 9/26 |
| Amigo | 0 | 1 | 70.66 | 9/17 |
| Pedro | 0 | 1 | 68.58 | 10/6 |
| Howard | 2 | 0 | 72.73 | 9/25 |
| Chandler | 1 | 1 | 74.01 | 10/14 |
| Cisco (UC 66-178) | 2 | 0 | 67.23 | 10/19 |
| Selections | | | | |
| UC 67-011 ("Tulare") | 1 | 3 | 65.41 | 10/1 |
| UC 67-013 | 2 | 1 | 77.85 | 9/24 |
| UC 76-080 | 0 | 0 | 84.44 | 10/19 |
| UC 77-012 | 5 | 2 | 43.55 | 9/27 |

[a]Relative Light Intensity
Other damage: mold, insects (Codling Moth and Navel Orange Worm), and black kernals.

I claim:

1. The new and distinct variety of walnut tree herein described and illustrated and identified by the characteristics enumerated above.

* * * * *